United States Patent

Schrader (10) Patent No.: US 9,782,120 B2
(45) Date of Patent: Oct. 10, 2017

(54) CANNULATED SCREW PROBE

(71) Applicant: Tim Schrader, Atlanta, GA (US)

(72) Inventor: Tim Schrader, Atlanta, GA (US)

( * ) Notice: Subject to any disclaimer, the term of this patent is extended or adjusted under 35 U.S.C. 154(b) by 654 days.

(21) Appl. No.: 14/268,667

(22) Filed: May 2, 2014

(65) Prior Publication Data

US 2014/0330135 A1 Nov. 6, 2014

Related U.S. Application Data

(60) Provisional application No. 61/818,732, filed on May 2, 2013.

(51) Int. Cl.
| | |
|---|---|
| A61B 5/02 | (2006.01) |
| A61B 5/00 | (2006.01) |
| A61B 5/0245 | (2006.01) |
| A61B 5/026 | (2006.01) |
| A61B 17/74 | (2006.01) |

(52) U.S. Cl.
CPC .......... *A61B 5/4571* (2013.01); *A61B 5/026* (2013.01); *A61B 5/0245* (2013.01); *A61B 5/6878* (2013.01); *A61B 17/742* (2013.01); *A61B 2505/05* (2013.01)

(58) Field of Classification Search
None
See application file for complete search history.

(56) References Cited

U.S. PATENT DOCUMENTS

| | | | | |
|---|---|---|---|---|
| 5,868,711 | A  * | 2/1999 | Kramer | A61B 17/3472 604/136 |
| 2002/0052605 | A1* | 5/2002 | Grooms | A61B 17/862 623/13.14 |
| 2005/0059979 | A1* | 3/2005 | Yetkinler | A61B 17/8822 606/92 |
| 2007/0049945 | A1* | 3/2007 | Miller | A61B 17/32002 606/86 R |
| 2009/0093818 | A1* | 4/2009 | Baroud | A61B 17/8816 606/93 |
| 2010/0152616 | A1* | 6/2010 | Beyhan | A61B 10/025 600/568 |
| 2010/0286507 | A1* | 11/2010 | Paassilta | A61B 5/053 600/424 |

OTHER PUBLICATIONS

Notzli et al. Perfusion of the femoral head during surgical dislocation of the hip: Monitoring by Laser Doppler Flowmetry. The Journal of Bone and Join Surgery [Br] 2002; 84-B:300-4.*

* cited by examiner

*Primary Examiner* — Etsub Berhanu
(74) *Attorney, Agent, or Firm* — Alston & Bird LLP (57) ABSTRACT

Concepts for measuring and monitoring characteristics of osseous tissue are presented. In various embodiments, a monitoring probe may be inserted through a hollow passageway within a cannulated screw during an operation in order to measure characteristics of the osseous tissue in which the cannulated screw is inserted. In various embodiments, the cannulated screw may be inserted into a femoral head, through a physis, and into an epiphysis for stabilization of Slipped Capital Femoral Epiphysis. During surgical treatment thereof, a pressure transducer may be inserted into the osseous tissue through the cannulated screw in order to monitor epiphysis perfusion through the femoral head.

9 Claims, 9 Drawing Sheets

CANNULATED SCREW PROBE

CROSS-REFERENCE TO RELATED APPLICATIONS

This patent application claims priority to Provisional Application Ser. No. 61/818,732, filed May 2, 2013, which is incorporated herein by reference in its entirety.

BACKGROUND

Figure 1:
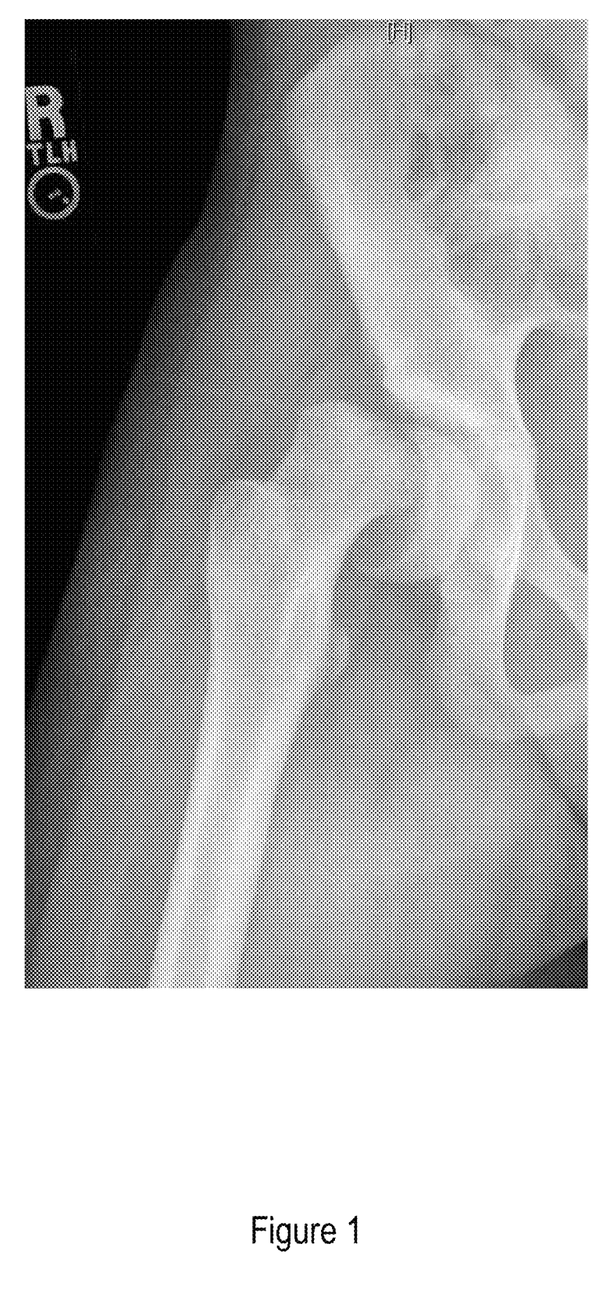
FIG. 1 illustrates an exemplary hip joint exhibiting Slipped Capital Femoral Epiphysis (SCFE)

Slipped Capital Femoral Epiphysis (SCFE) is a common adolescent hip disorder where the capital femoral epiphysis may be displaced posteroinferior relative to the metaphysis. SCFE may occur along the physis (also referred to as the growth plate) of the femoral head near a patient's hip joint. An exemplary instance of SCFE is illustrated in FIG. 1. Patients having SCFE may exhibit symptoms such as limping, inability to bear weight on the affected extremity, or hip, knee, or thigh pain. Patients with sudden and severe hip pain who cannot bear weight on the affected extremity, even with crutches, are classified as having unstable SCFE. In some cases, patients with SCFE may develop osteonecrosis of the femoral head after surgical treatment to repair or mitigate the effects of SCFE. The overall incidence of osteonecrosis associated with unstable SCFE is unknown, with estimates ranging from 10%-60% in literature. Due to the potentially high association between SCFE and osteonecrosis, many authors considering the issue have advocated for early treatment of unstable SCFE (typically within 24 hours of the onset of symptoms).

Particularly for unstable instances of SCFE, treatment often requires surgical intervention and insertion of one or more cannulated screws into the femoral head, through the physis, and into to femoral epiphysis in order to stabilize the osseous tissue and prevent further slippage of the tissue relative to the metaphysis. As is understood by those skilled in the art, cannulated screws have a hollow shaft forming a central passageway running longitudinally along the length of the screw. In certain instances, the screw may include one or more thread patterns along at least a portion of the exterior surface of the screw, and may include a screw head being formed by a portion of the screw, measured longitudinally, located at the end of the screw opposite the threaded end. As will be understood, the screw head may have an outer diameter larger than the diameter of the remainder of the cannulated screw. Currently, cannulated screws are often utilized in the treatment of SCFE by stabilizing the slipping epiphysis, and to stabilize bone fractures in joints, among other treatments.

Many considering the issue have hypothesized that increased intracapsular pressure and/or kinking of lateral epiphyseal vessels may lead to the disruption of the femoral head blood supply in unstable instances of SCFE. In certain instances, treatment of SCFE may include a capsulotomy procedure to relieve pressure in the femoral head and therefore decrease the likelihood of osteonecrosis in the joint. Therefore, methods and devices for intra-operatively monitoring the femoral head blood supply (epiphyseal perfusion) and epiphyseal pressure in patients with SCFE are needed to better understand the relationships between intracapsular pressure, epiphyseal perfusion, and the occurrence of osteonecrosis.

BRIEF SUMMARY

In various embodiments, a method for monitoring osseous tissue characteristics is provided. The method comprises steps for: (1) inserting a cannulated screw such that at least a portion of the cannulated screw extends through a first osseous region and into a second osseous region, wherein the cannulated screw comprises a body and a passageway extending longitudinally from a first end of the body to a second end of the body; (2) inserting a measurement probe into the second osseous region through the passageway of the cannulated screw; and (3) measuring osseous tissue characteristics of the second osseous region using the inserted measurement probe.

In alternative embodiments, a system for monitoring osseous tissue characteristics is provided comprising: (1) a cannulated screw comprising a body having a passageway formed therein extending longitudinally from a first end of the body to a second end of the body, wherein the body includes a head portion proximate the first end and a threaded portion, and configured for insertion into the osseous tissue; (2) a measurement probe configured to be inserted into the passageway formed in the cannulated screw and to sense a measured characteristic in the osseous tissue; and (3) a display device in communication with the measurement probe and configured to display the measured characteristic such that the presence of perfusion within the osseous tissue can be determined.

BRIEF DESCRIPTION OF THE SEVERAL VIEWS OF THE DRAWINGS

Reference will now be made to the accompanying drawings, which are not necessarily drawn to scale, and wherein.

DETAILED DESCRIPTION

The present invention will now be described more fully hereinafter with reference to the accompanying drawings, in which some, but not all embodiments of the invention are shown. Indeed, the invention may be embodied in many different forms and should not be construed as limited to the embodiments set forth herein. Rather, these embodiments are provided so that this disclosure will satisfy applicable legal requirements. Like numbers refer to like elements throughout.

Overview

In various embodiments, methods and systems are described for monitoring characteristics of osseous tissue intra-operatively. Specifically, the method may include steps for insertion of a sterilized cannulated screw into the femoral head in order to stabilize the epiphysis, and may include the additional step of inserting a probe through the passageway of the cannulated screw to monitor at least one characteristic of the osseous tissue in which the cannulated screw is inserted. For example, the method may include the steps of (1) inserting a guide wire into osseous tissue, (2) inserting a cannulated screw at least partially into the osseous tissue using the guide wire, (3) removing the guide wire, (4) inserting a probe (e.g., a pressure transducer) into the cannulated screw until the inserted end of the probe extends into the osseous tissue beyond the inserted end of the cannulated screw, (5) monitoring at least one characteristic of the osseous tissue (e.g., intracapsular pressure), (6) removing the probe, and (7) advancing the screw to the fully seated position in the drilled hole.

Monitoring Osseous Tissue Characteristics

Referring now to FIGS. 2-7, methods for monitoring characteristics of osseous tissue will now be described. In various embodiments, the described method may be utilized to monitor the epiphysis perfusion in the femoral head during operative treatment for SCFE by insertion of a probe beyond a physis. As will be understood however, the described method may be utilized to intra-operatively monitor characteristics of any osseous tissue by insertion of a monitoring probe into the osseous tissue beyond any osseous interface. As non-limiting examples, an osseous interface may be embodied as a physis between an epiphysis and metaphysis; a fracture line or plane between two similar osseous regions; and/or the like. In various embodiments, a percutaneous SCFE screw fixation technique utilizing a radiolucent table and supine positioning may be utilized.

Figure 2:
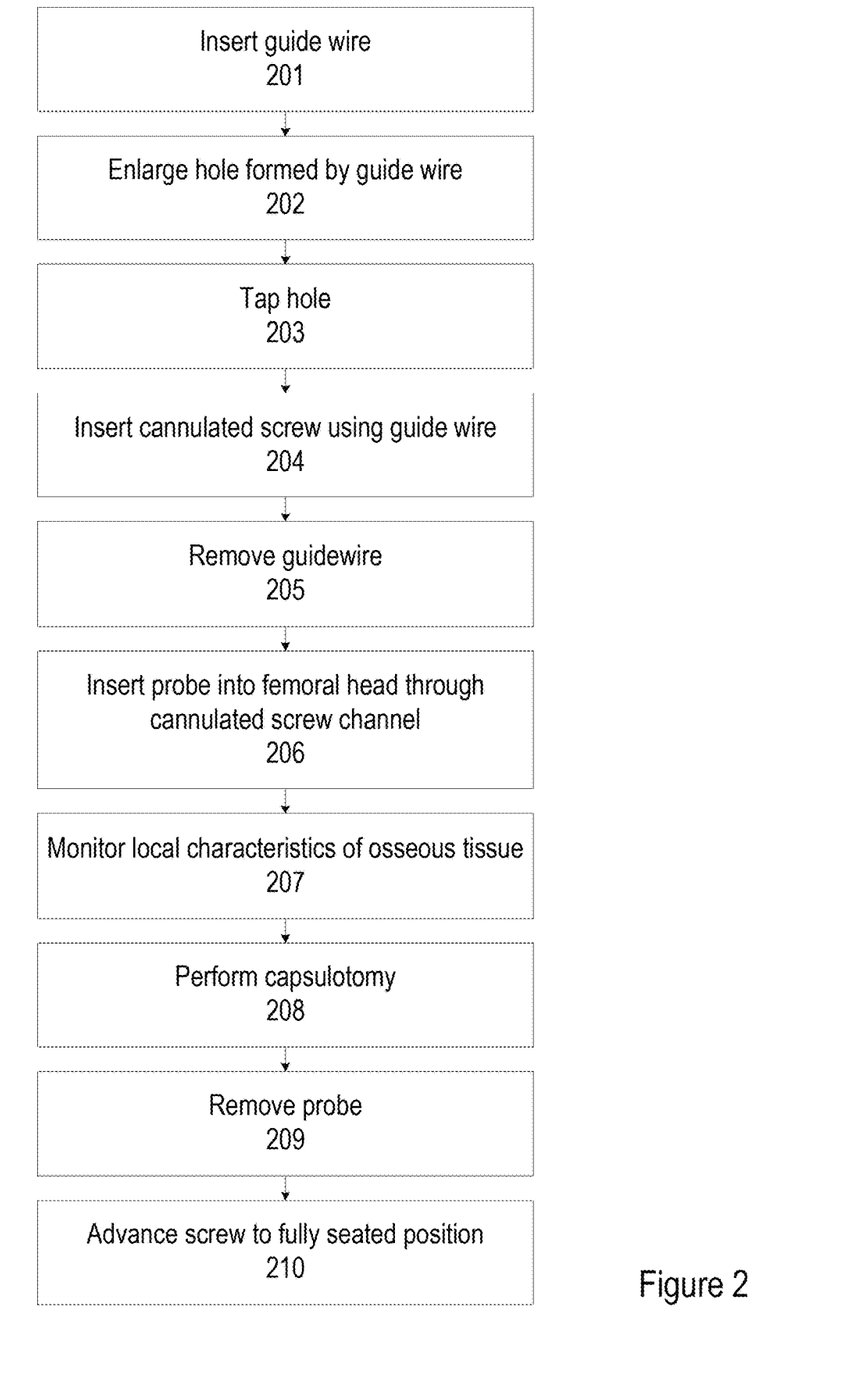
FIG. 2 is a flow chart illustrating the various steps included in a method according to one embodiment.
Figure 3:
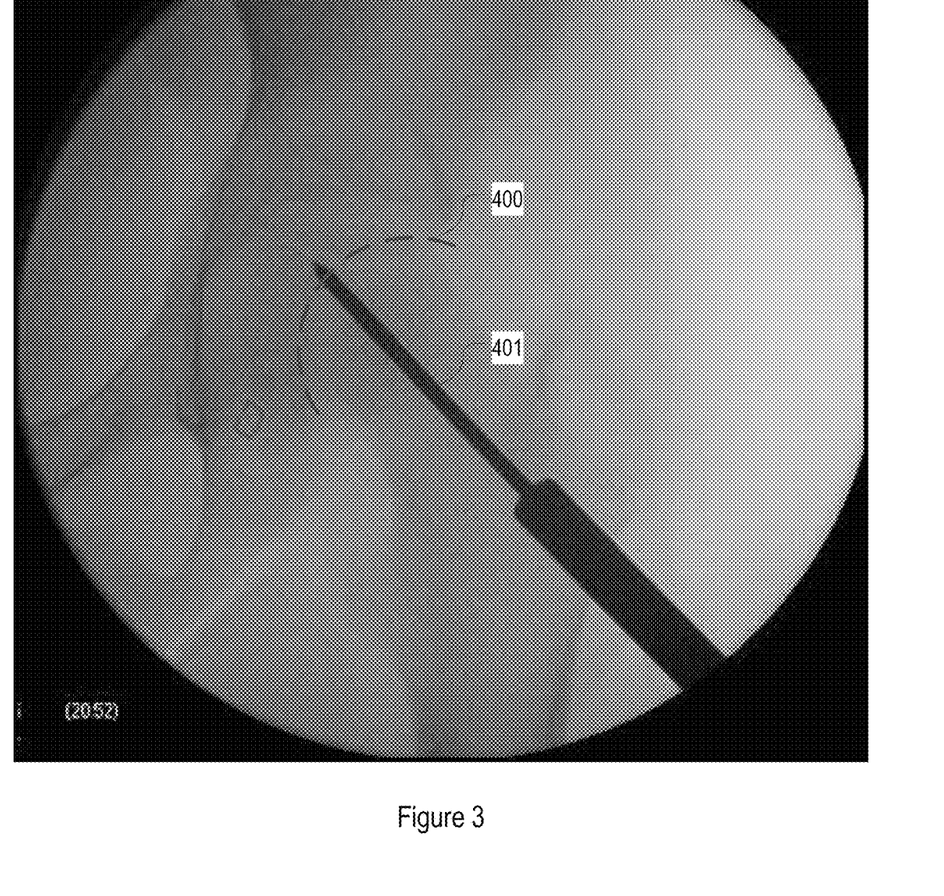
FIG. 3 illustrates a guide wire inserted beyond an osseous interface according to one embodiment of the present invention.

Referring to FIGS. 2 and 3, the method begins at step 201 by inserting a guide wire 401 into the osseous region (e.g., a femoral head), through the osseous interface (e.g., a physis) 400, and at least partially into the second osseous region (e.g., an epiphysis). Guide wire insertion may be accomplished using methods known to those skilled in the art, such as by drilling the guide wire into position. As will be understood by one skilled in the art, the depth of insertion may be determined at least in part on a determination of the required depth needed to insert a cannulated screw 402 into the second osseous region in order to stabilize the instance of SCFE. The guide wire 401 may serve to guide a cannulated drill bit, a tap, and/or the cannulated screw 402 into proper position during insertion into the osseous tissue, and may be used to facilitate measurement of the depth of insertion of a cannulated screw. As shown in FIG. 3, the guide wire 401 may be inserted into the femoral head through the metaphysis, beyond the osseous interface (shown in FIG. 3 as the physis) 400, and into the second osseous region.

At step 202 of FIG. 2, a drill bit (not shown) may be used to enlarge the diameter of the hole formed by the guide wire 401. In various embodiments, the drill bit may be embodied as a cannulated drill bit configured to fit over the guide wire 401 as it is enlarging the hole. As will be understood by one skilled in the art, the drill bit may be sized to create a hole large enough for the insertion of the cannulated screw 402. In various embodiments, at step 203 a tap (not shown) may be inserted to tap threads into the wall of the hole formed by the drill bit. In various embodiments, the tap may be embodied as a cannulated tap configured to fit over the guide wire 401. As will be understood by one skilled in the art, the tap may be used to form threads that match the threads on the cannulated screw 402. As will be understood by one skilled in the art, self-drilling and/or self-tapping cannulated screws may be utilized and the steps of enlarging and tapping the hole formed by the guide wire may be combined with the following step of inserting the cannulated screw 402.

Figure 4:
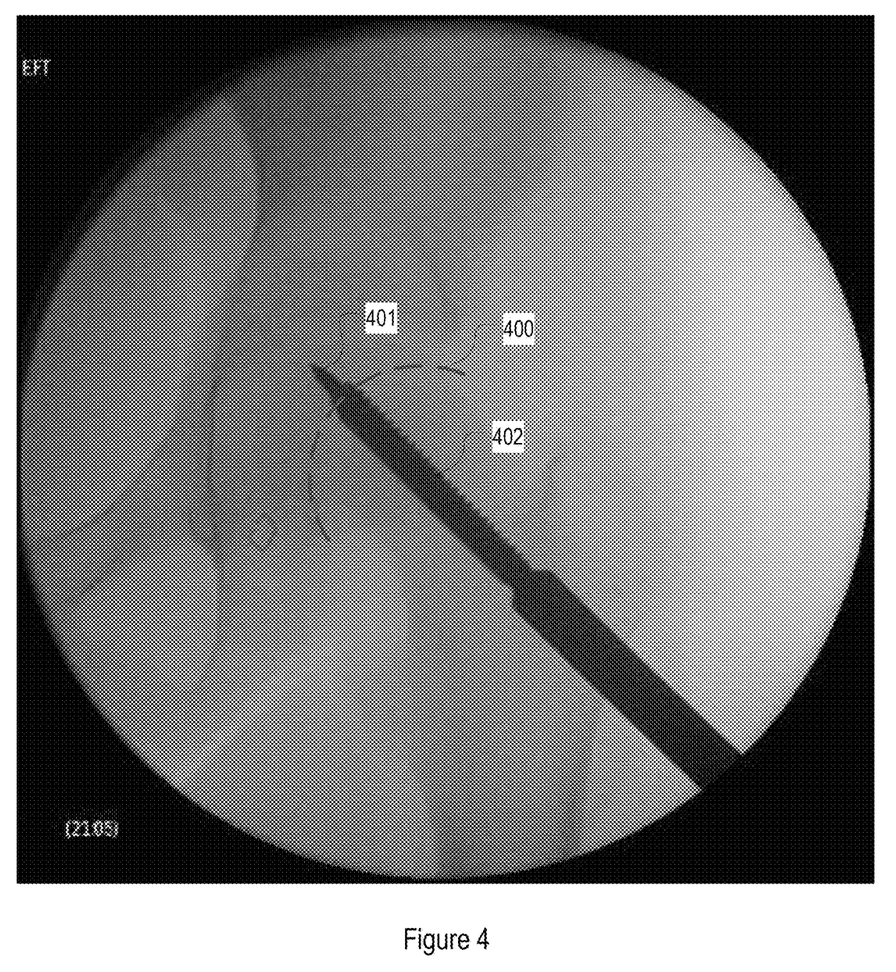
FIG. 4 illustrates a cannulated screw inserted over a guide wire according to one embodiment of the present invention.

As shown in FIGS. 2 and 4, at step 204, a cannulated screw 402 may be inserted into the osseous tissue along the guide wire 401. In various embodiments, a fully or partially threaded cannulated screw may be utilized. As a non-limiting example, a stainless steel 7.0 mm Richards screw may be utilized, although other materials, sizes, and types of cannulated screws may be utilized. Because the cannulated screw 402 has a hollow central passageway, the cannulated screw may be inserted over the guide wire 401 such that the guide wire 401 facilitates the insertion of the cannulated screw into the proper position. A cannulated screw 402 inserted over a guide wire 401 is shown in FIG. 4. As shown in FIG. 4, the cannulated screw 402 may be advanced beyond the osseous interface (e.g., the physis) 400. This may provide stabilization of the osseous tissue, such as a hip exhibiting SCFE. In various embodiments, the cannulated screw 402 may not be advanced to its fully seated position, at which the cannulated screw 402 remains following the surgical operation. As shown in FIG. 4, the cannulated screw 402 may be inserted such that the inserted end extends beyond the osseous interface 400 and into the second osseous region, but the cannulated screw 402 is not advanced to the same depth as the guide wire 401. Leaving some distance between the inserted end of the cannulated screw 402 and the end of the hole formed by the guide wire 401 allows an inserted probe 403 to extend into the osseous region beyond the end of the cannulated screw 402 once the guide wire 401 is removed.

Figure 5:
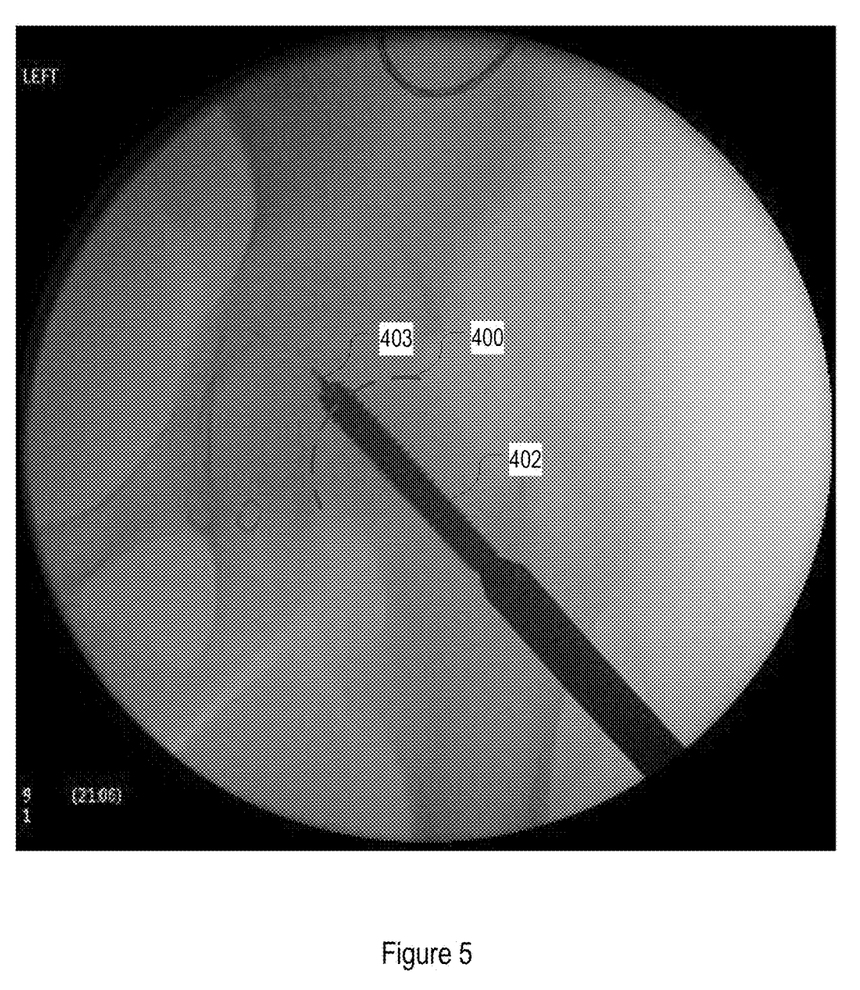
FIG. 5 illustrates a probe inserted through a cannulated screw according to one embodiment of the present invention.

The guide wire 401 may be removed from the osseous tissue and cannulated screw 402 at step 205 of FIG. 2. In various embodiments, a screw driver may remain engaged with the cannulated screw 402 after removal of the guide wire 401. By removing the guide wire 401, a probe or other object may be inserted into the osseous tissue through the passageway in the cannulated screw 402. As will be understood by one skilled in the art, by removing the guide wire 401, the hollow space in the osseous tissue formed by the guide wire 401 may fill with fluid. As shown in FIG. 5, a probe 403 may be inserted into the hollow space in the osseous tissue formed by the guide wire 401 through the passageway in the cannulated screw 402 at step 206. In various embodiments, the probe 403 may be a pressure transducer, such as an Integra Camino ICP pressure transducer used in combination with a monitoring device such as an Integra pressure monitor. In various embodiments, the probe 403 may comprise a strain gauge pressure transducer or light refraction pressure transducer such as those known in the art. The monitoring device may comprise a monitoring device such as those generally known in the art, being in communication with a display device that may be utilized to display measured characteristic data (e.g., measured osseous tissue characteristic data) recorded by the probe 403. As will be understood by one skilled in the art, the monitoring device may comprise one or more display devices, or the monitoring device may be in communication with one or more external display devices. Any type of probe may be used, including, for example, probes used for measuring oxygen levels, temperature, and/or other parameters.

Figure 7:
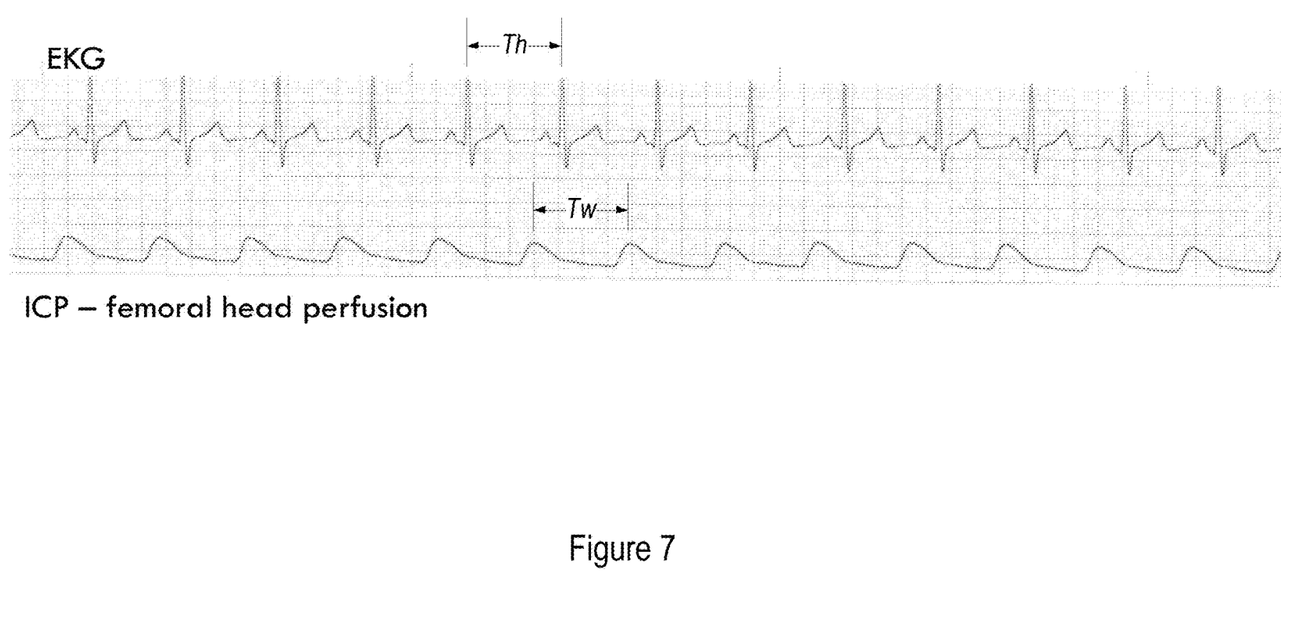
FIG. 7 illustrates an EKG output and ICP output according to various embodiments of the present invention.
Figure 8A:
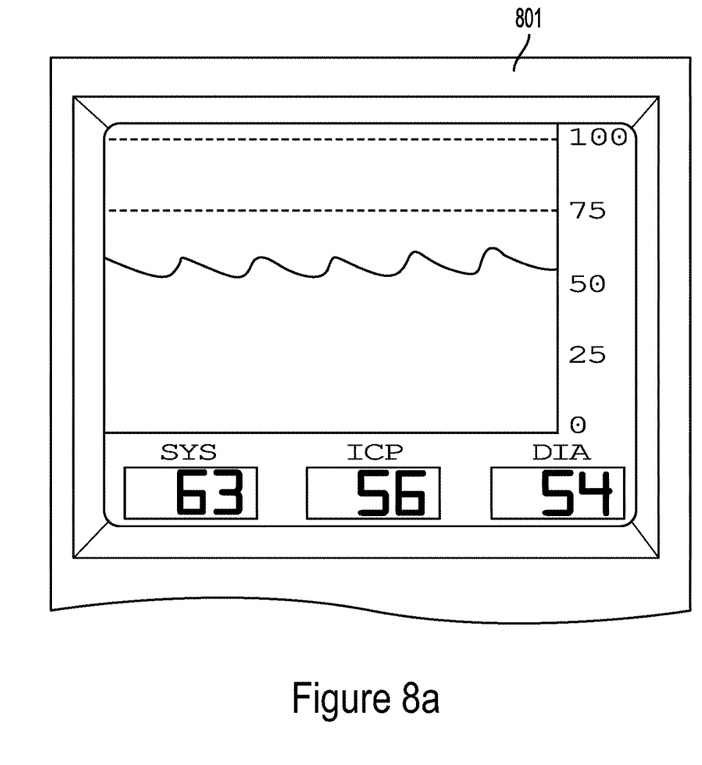
FIGS. 8a-8c illustrate exemplary display devices according to one embodiment of the present invention.
Figure 8B:
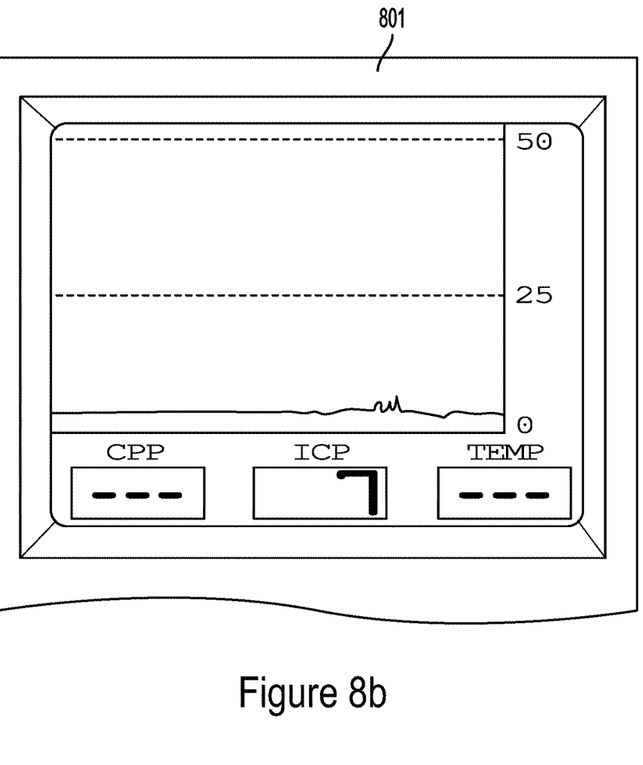
Figure 8C:
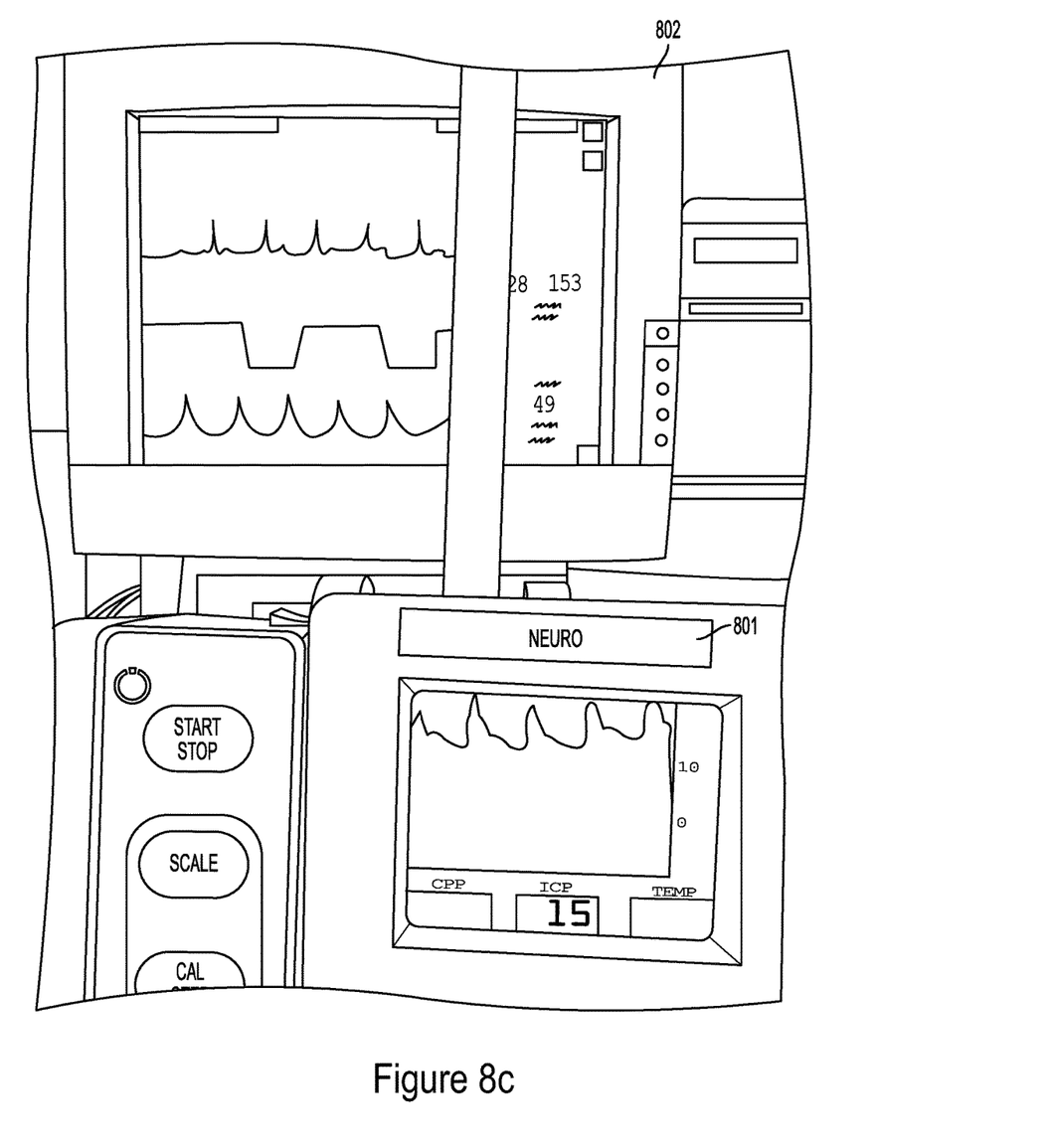

At step 207, the inserted probe 403 may be utilized to measure characteristics of the osseous tissue, such as epiphyseal perfusion pressure in a femoral head. The inserted probe 403 may be in communication with the monitoring device, and may transmit measured characteristic data corresponding to the measured characteristics (e.g., measured osseous tissue characteristics) to the monitoring device. In various embodiments, a pressure transducer may be utilized to capture intra-operative perfusion pressure data, and at least a portion of these measured characteristic data may be transmitted to a monitoring device and subsequently displayed on a display device in communication with the monitoring device, as shown in FIGS. 8a-8c, or printed as an output, as shown in FIG. 7. As a non-limiting example, at least a portion of the measured characteristic data may be displayed graphically as an osseous tissue characteristic waveform or as a value indicative of the measured characteristic. For example, the epiphyseal perfusion pressure evident in the fluid present in the hollow space in the osseous tissue formed by the guide wire 401 may be measured by the probe 403, which may transmit measured characteristic data corresponding to the epiphyseal perfusion pressure to the monitoring device, and the measured characteristic data may be displayed graphically via a display device 801 in communication with the monitoring device, as illustrated in FIGS. 8a-8c. As will be understood by those skilled in the art, the state of the osseous tissue characteristics measured intra-operatively may provide evidence of the state of the osseous tissue characteristics occurring pre- and/or post-operatively. The measured characteristic data may be displayed as a function of the measured osseous tissue characteristic over time (e.g., as a waveform). As described herein, the patient's heart rate may also be monitored using an electrocardiogram (EKG) machine or other suitable apparatus, and using methods known to those skilled in the art. In various embodiments, heart rate data corresponding to a patient's heart rate obtained during the measurement process may be collected and displayed using a display device 802 in communication with a heart rate monitoring device, as shown in FIG. 8c. The heart rate data may be displayed graphically as a function of time, as shown in FIG. 7. The heart rate data and the measured characteristic data may be displayed using a single display device or using multiple display devices. As a non-limiting example, the measured characteristic data collected intra-operatively may comprise pulse pressure data having an osseous tissue characteristic waveform that is substantially synchronous with the patient's heart rate. As a non-limiting example, patient hips exhibiting stable SCFE, prophylactically treated hips, and some hips exhibiting unstable SCFE may have measurable, pulsated flow with the initial insertion of the probe. FIGS. 7, 8a, and 8c illustrate exemplary EKG output and ICP output showing measurable, pulsated flow within the epiphysis. As shown in FIG. 7, the pulsatile waveform corresponding to the measured characteristic data collected by the probe 403 may be at least substantially synchronous with the patient's heart rate in instances wherein epiphysis perfusion is present throughout the femoral head. In various embodiments in which the waveform corresponding to the measured characteristic data collected by the probe 403 is substantially synchronous with the patient's heart rate, the osseous tissue characteristics waveform period Tw may be at least substantially equivalent to the patient's heart rate period Th. However, some hips having unstable SCFE may have no measurable flow within the epiphysis and therefore the measured characteristic data may present a substantially flat waveform as measured by the probe 403, as illustrated by FIG. 8b. For those patient hips exhibiting no measurable flow, one or more capsulotomy procedures, or other appropriate procedures, may be performed in an attempt to establish a measurable epiphysis perfusion. In various embodiments, some hips may have measurable flow establishing a waveform that is not substantially synchronous with the patient's heart rate, such that the osseous tissue characteristics waveform period Tw may not be substantially equivalent to the patient's heart rate period Th. Measured characteristic data having waveforms that are not substantially synchronous with the patient's heart rate may be evidence of the probe 403 being placed incorrectly within the osseous tissue. However, measured characteristic data having waveforms that are not substantially synchronous with the patient's heart rate may also be evidence of other issues, and appropriate measures may be undertaken to correct these issues.

Referring back to FIG. 2, at step 208 a surgeon may utilize the measured characteristic data to tailor the procedure for the specific patient. As a non-limiting example, if the measured characteristic data does not demonstrate a measurable blood flow within the epiphysis, the surgeon may perform one or more capsulotomy procedures to relieve pressure within the femoral head in an attempt to create measurable epiphysis perfusion within the monitored region of osseous tissue. However, in patient hips exhibiting a measurable flow, the surgeon need not perform any additional steps in an attempt to create a measurable flow within the femoral head, and in such instances the method may omit step 208.

Figure 6:
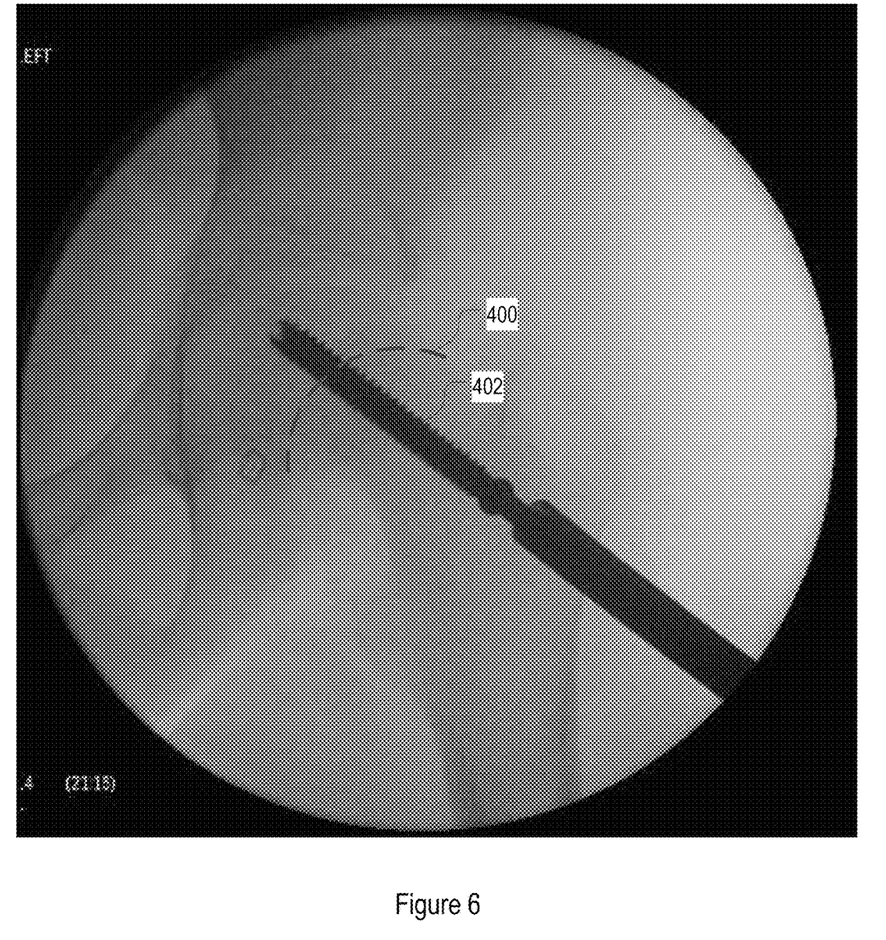
FIG. 6 illustrates a cannulated screw in its fully seated position according to one embodiment of the present invention.

After completion of the monitoring step, the probe 403 may be removed from the osseous tissue through the cannulated screw 402 at step 209. In various embodiments, the guide wire 401 may be reinserted into the osseous tissue through the cannulated screw 402. In procedures wherein the cannulated screw 402 will remain in the osseous tissue, the cannulated screw 402 may be advanced to its fully seated position at step 210. FIG. 6 illustrates a cannulated screw 402 in its fully seated position in which a portion of the cannulated screw extends beyond the osseous interface (shown in FIG. 6 as the physis) 400 in order to stabilize the osseous tissue.

As will be understood by one skilled in the art, one or more steps in the above described method may be performed in any order, and/or simultaneously. The order in which the steps of the above described method are described is not necessarily indicative of the order in which the steps must be performed. Moreover, as will be understood by one skilled in the art, the method may include a step of drilling the insertion hole without utilizing a guide wire, such that a self-drilling and/or self-tapping cannulated screw need not be utilized. Although the method described above was noted as being applicable to treatment of SCFE by stabilizing the epiphysis using a cannulated screw inserted beyond the physis, it should be understood by one skilled in the art that the above described method may be utilized in any operation utilizing a cannulated screw advanced into one or more osseous regions. For example, the above described method may be utilized to measure pressure or perfusion within an osseous region near a bone fracture. In such instances, a cannulated screw may be advanced through a first osseous region, beyond the osseous interface, and into a second osseous region. The method may therefore be used to measure characteristics of the osseous tissue located in the second osseous region.

System for Monitoring Osseous Tissue Characteristics

In various embodiments, the method described herein may be performed by a system configured for monitoring osseous tissue characteristics. The system may be embodied as a physical apparatus, and may be a component of one or more monitoring devices utilized during the described method. However, as will be understood by one skilled in the art, the system for monitoring osseous tissue characteristics may be embodied in a device or computer program product separate from and in communication with the monitoring device utilized in the described method.

In various embodiments, the system for monitoring osseous tissue characteristics may comprise a probe 403 configured for insertion through a cannulated screw 402, a monitoring device, a heart rate monitoring device, and one or more display devices (801, 802) in communication with the monitoring device and the heart rate monitoring device. As described above, the monitoring device may comprise one or more display devices, or the monitoring device may be in communication with one or more external display devices. The monitoring device of the system for monitoring osseous tissue characteristics may include components configured for receiving measured characteristic data (e.g., pressure data) captured by the probe 403, and heart rate data collected from the heart rate monitoring device. The probe 403 may be in communication with the monitoring device, and may be configured to transmit measured characteristic data (e.g., pressure data) to the monitoring device. In various embodiments, the EKG machine may be configured to transmit heart rate data to a display device 802 and cause display of the heart rate data. Moreover, the monitoring device may be configured to transmit at least a portion of the measured characteristic data to a display device 801 and cause display of the measured characteristic data. In various embodiments, the system for monitoring osseous tissue characteristics may be configured to compare at least a portion of the measured characteristic data and the heart rate data to determine whether the measured characteristic data suggests perfusion is present within the osseous tissue. As a non-limiting example, patient hips exhibiting stable SCFE, prophylactically treated hips, and some hips exhibiting unstable SCFE may have measurable, pulsated perfusion with the initial insertion of the probe into the epiphysis of a femoral head. FIG. 7 illustrates an exemplary EKG output and ICP output showing measurable, pulsated flow within the epiphysis. As shown in FIG. 7, the pulsatile waveform representative of the measured characteristic data captured by the probe 403 may be at least substantially synchronous with the patient's heart rate in instances wherein perfusion is present throughout the epiphysis. In various embodiments in which the measured characteristic data captured by the probe 403 is substantially synchronous with the patient's heart rate, the osseous tissue characteristics waveform period Tw may be at least substantially equivalent to the patient's heart rate period Th, as shown in FIG. 7. However, some hips having unstable SCFE may have no measurable flow within the epiphysis. For those patient hips exhibiting no measurable flow, a capsulotomy may be performed in an attempt to create measurable epiphysis perfusion.

As will be understood by one skilled in the art, various embodiments of osseous tissue characteristic monitoring method and system have applications beyond the treatment of SCFE. The described techniques for inserting probes through a cannulated screw may be used for other measurement devices, such as those configured for measuring oxygenation levels, temperature, and other parameters within osseous tissue. In various embodiments, the devices may be mechanical or optical. Furthermore, these techniques may be used to measure parameters in any bone in the body. As a non-limiting example, these techniques may be applicable to the orthopedic trauma setting where cannulated screw fixation might be indicated for a particular fracture pattern. In such settings, the steps described above for inserting a guide wire, drill bit, tap, and/or a cannulated screw beyond a physis may be completed by inserting the guide wire, drill bit, tap, and/or cannulated screw beyond an osseous interface. Non-limiting examples of such fracture sites may include the talar neck, femoral neck, proximal humerus, and scaphoid waist. By placing the pressure probe through the cannulated screw and into the osseous tissue believed to be at risk of developing osteonecrosis, the pressure probe and monitoring system may record and display a real-time representation of blood flow within the measured region of osseous tissue. If the pressure monitoring system indicates poor flow, a surgeon may tailor the operative plan appropriately (i.e., the plan may be changed from a cannulated screw fixation procedure to a hemiarthroplasty for an elderly patient with a femoral neck fracture). The data gathered from intra-operative pressure monitoring may also allow the surgeon to more accurately prognosticate outcomes and counsel the patient accordingly.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for monitoring osseous tissue characteristics, the method comprising the steps of:
   inserting a cannulated screw such that at least a portion of the cannulated screw extends through a first osseous region and into a second osseous region, wherein the cannulated screw comprises a body and a passageway extending longitudinally from a first end of the body to a second end of the body;
   inserting a measurement probe into the second osseous region through the passageway of the cannulated screw;
   measuring osseous tissue characteristics of the second osseous region using the inserted measurement probe;
   recording waveforms in the measured osseous tissue characteristics via an osseous tissue monitoring device in electronic communication with the measurement probe;
   measuring a heart rate via a heart rate monitoring device;
   recording a heart rate waveform via the heart rate monitoring device;
   comparing, via the osseous tissue monitoring device, the heart rate waveform to an osseous tissue characteristics waveform; and
   determining, via the osseous tissue monitoring device, the presence of perfusion in the second osseous region based on the comparison between the heart rate waveform and the osseous tissue characteristics waveform.

2. The method of claim 1, wherein the second osseous region comprises an epiphysis region located in a femoral head.

3. The method of claim 1, wherein the osseous tissue characteristics comprise at least one of pressure, temperature, or oxygen level.

4. The method of claim 1, further comprising the step of:
   inserting a guide wire such that at least a portion of the guide wire extends through the first osseous region and into the second osseous region; and after inserting the cannulated screw, removing the guide wire; and wherein the cannulated screw is positioned based at least in part on the guide wire.

5. The method of claim 1, wherein the heart rate waveform comprises a heart rate period and the osseous tissue characteristics waveform comprises an osseous tissue characteristics waveform period; and the comparing step comprises the step of comparing the heart rate period and the osseous tissue characteristics waveform period and determining if the heart rate period and waveform period are substantially equivalent.

6. The method of claim 1, further comprising the steps of:

if the comparison step indicates that perfusion is not present in the second osseous region, performing an operation to establish perfusion in the second osseous region; and measuring the osseous tissue characteristics of the second osseous region after performing the operation.

7. A system for monitoring osseous tissue characteristics comprising:

a cannulated screw comprising a body having a passageway formed therein extending longitudinally from a first end of the body to a second end of the body, wherein the body includes a head portion proximate the first end and a threaded portion and configured for insertion into osseous tissue;

a measurement probe configured to be inserted into the passageway formed in the cannulated screw and to sense characteristics in the osseous tissue;

a heart rate monitoring device configured to measure a heart rate period;

a monitoring device configured to:

record waveforms in the characteristics of the osseous tissue, wherein the waveforms comprise a waveform period;

compare the heart rate period and one of the waveform periods; and determine if the heart rate period and the waveform period are at least substantially equivalent; and a display device in communication with the measurement probe and configured to display the characteristics such that the presence of perfusion within the osseous tissue can be determined.

8. The system of claim 7, wherein the cannulated screw is configured for insertion into a femoral head and the measurement probe is configured to sense characteristics of epiphysis tissue located in a femoral head.

9. The system of claim 7, wherein the characteristics of osseous tissue comprise at least one of: a pressure, a temperature, and an oxygen level.

* * * * *